United States Patent
Yagi et al.

(10) Patent No.: US 6,169,211 B1
(45) Date of Patent: Jan. 2, 2001

(54) PROCESS AND APPARATUS FOR PRODUCTION OF 5-CYCLOHEXADECEN-1-ONE

(75) Inventors: Misao Yagi; Keisuke Itakura; Kenichi Yamamoto; Akira Amano, all of Hiratsuka (JP)

(73) Assignee: Takasago International Corporation, Tokyo (JP)

( * ) Notice: Under 35 U.S.C. 154(b), the term of this patent shall be extended for 0 days.

(21) Appl. No.: 09/304,256

(22) Filed: May 6, 1999

(30) Foreign Application Priority Data

May 7, 1998 (JP) .................................................. 10-124717

(51) Int. Cl.[7] .................................................. C07C 49/547
(52) U.S. Cl. .......................... 568/343; 568/375; 422/129; 201/29; 203/88; 203/91
(58) Field of Search ..................................... 568/338, 361, 568/375, 343; 422/189, 225, 129; 201/29; 203/88, 91

(56) References Cited

U.S. PATENT DOCUMENTS 3,929,893 * 12/1975 Kumasa et al. .................. 260/586 R

FOREIGN PATENT DOCUMENTS 51-004148 * 1/1976 (JP) .

* cited by examiner

Primary Examiner—Sreeni Padmanabhan
(74) Attorney, Agent, or Firm—Kubovcik & Kubovcik

(57) ABSTRACT

Disclosed is a process for producing 5-cyclohexadecen-1-one continuously from 1,2-divinylcyclododecanol in a short time in an efficient manner without side reactions. In the process, 1,2-divinylcyclododecanol as a starting material is supplied from a raw material container 1 by a dosage pump 2 to a flash unit 3 which is set under a vacuum of 5 mm Hg or less by a vacuum pump 8 and is heated. 1,2-Divinylcyclododecanol which is flashed in the flash unit is supplied to a reactor 4 which is heated to 400 to 650° C. and is set under a vacuum of 5 mm Hg or less whereby 1,2-divinylcyclododecanol is converted into 5-cyclohexadecen-1-one. The reaction product is discharged from the top of the reactor and is cooled to recover the objective 5-cyclohexadecen-1-one in the recovery container 6. The reduction in the pressure of the apparatus is preferably performed by a vacuum pump 8 via a hydrochloric acid trap 7 comprising, for example, sodium methylate/methanol cooled to −78 to −100° C.

21 Claims, 2 Drawing Sheets

PROCESS AND APPARATUS FOR PRODUCTION OF 5-CYCLOHEXADECEN-1-ONE

This invention relates to a novel process and apparatus for the production of a 5-cyclohexadecen-1-one, and, particularly to a process and apparatus for producing a 5-cyclohexadecen-1-one from 1,2-divinylcyclododecanol by an oxy-cope reaction.

BACKGROUND OF THE INVENTION

5-Cyclohexadecen-1-one has a relatively strong musk fragrance and is well-known as a compound useful for a starting material of perfumes. This 5-cyclohexadecen-1-one is generally produced according to the following chemical reaction:

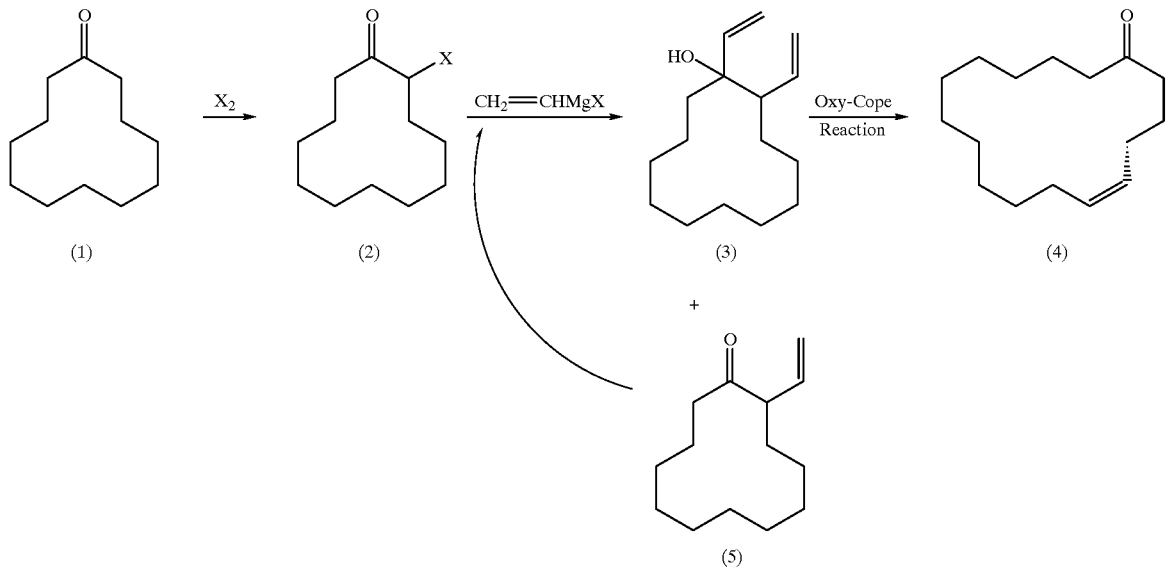

wherein X represents a halogen atom.

First, cyclododecanone (1) is halogenated to synthesize 2-halogenocyclododecanone (2). The resulting 2-halogenocyclododecanone (2) is reacted with vinyl magnesium Grignard to produce 1,2-divinylcyclododecanol (3), which is then converted into 5-cyclohexadecen-1-one (4) by an oxy-cope reaction, followed by refining to obtain the objective 5-cyclohexadecen-1-one.

1,2-divinylcyclododecanol (3) embraces a cis-isomer and a trans-isomer. The trans-isomer is quantitatively converted into 5-cyclohexadecen-1-one whereas the cis-isomer is accompanied by a side reaction and hence is not quantitatively converted into 5-cyclohexadecen-1-one. The reaction rate of the trans-isomer is larger than that of the cis-isomer. Accordingly, the theoretical yield in the early stage of the reaction of the trans-isomer is almost 100%. However, the theoretical yield decreases with the progress of the reaction.

In the reaction of 2-halogenocyclododecanone (2) with vinyl magnesium Grignard, 2-vinylcyclododecanone (5) is produced together with 1,2-divinylcyclododecanol (3). Since 1,2-divinylcyclododecanol (3) is produced through 2-vinylcyclododecanone (5), the by-production can be restrained with difficulty. If the 2-vinylcyclododecanone (5) is reacted again with the vinyl magnesium Grignard's reagent, it is easily converted into the objective 1,2-divinylcyclododecanol (3). The 2-vinylcyclododecanone (5) is however highly reactive so that it is easily resinified or isomerized into unacceptable ethylidene ketone.

Conventionally, the oxy-cope reaction such as described is usually carried out by heating the reaction raw material as it is or after it is dissolved in a solvent (for instance, Tetrahedron Letters No. 7, pp. 509–512, 1970). Accordingly, when 5-cyclohexadecen-1-one (4) is produced from 1,2-divinylcyclododecanol (3), a similar oxy-cope method is conventionally used. For instance, Japanese Patent Publication (JP-B) No. S52-42787 discloses a method in which 1,2-divinylcyclododecanol is heated either using no solvent or in an appropriate solvent at a temperature of 180–250° C. in a flowing inert gas for about 3 hours to produce 5-cyclohexadecen-1-one. JP-B No. S55-34781 reveals a method in which refined or unrefined 1,2-divinylcyclododecanol in a liquid state is heated either as it is or after it is dissolved in a solvent to produce 5-cyclohexadecen-1-one. JP-B No. S52-39025 reports a method in which 1,2-divinylcyclododecanol is heated in the presence of N,N-disubstituted carboxylic acid amides, N-substituted lactams or sulfoxides to produce 5-cyclohexadecen-1-one. JP-B No. S58-13528 suggests a method in which 1,2-divinylcyclododecanol is heated in the presence of a specific phosphorus compound to produce 5-cyclohexadecen-1-one.

These known manufacturing methods give the objective 5-cyclohexadecen-1-one in high yields. However, heat treatment at 150–350° C. for several hours is required to sufficiently complete the reaction. This reaction time is rather long. Also, since the reaction is a batch-type reaction, the production efficiency is poor. When a solvent is used, the cost increases. In addition, the solvent must be removed after the reaction is completed and it is necessary to recover the objective product by distillation under reduced pressure. In conventionally known methods, negative side reactions are also caused. For instance, when the oxy-cope reaction is made using unrefined 1,2-divinylcyclododecanol as a starting material, 2-vinylcyclododecanone which was contained in the starting material as an impurity is isomerized into ethylidene ketone by heat treatment.

SUMMARY OF THE INVENTION

Objects of the present invention are to provide a process for producing a 5-cyclohexadecen-1-one and an apparatus used for the process. The process is characterized in that it has no problems such as those involved in the conventional processes for the production of 5-cyclohexadecen-1-one, can produce 5-cyclohexadecen-1-one in a short reaction time in a high yield, can improve the production efficiency by simplifying the production process and making the process steps continuous and gives rise to no reactions other than the oxy-cope reaction when 1,2-divinylcyclododecanol is converted into 5-cyclohexadecen-1-one.

The inventors of the present invention have made earnest studies to attain the above objects and, as a result, found that the prior art problems can be solved by heating 1,2-divinylcyclododecanol in the vapor phase at high temperatures under reduced pressure to complete the invention.

According to a first embodiment of the present invention, there is provided a process for producing a 5-cyclohexadecen-1-one comprising heating 1,2-divinylcyclododecanol in the vapor phase at 400 to 650° C. under reduced pressure.

According to a second embodiment of the present invention, there is provided a process for producing a 5-cyclohexadecen-1-one comprising heating a liquid raw material containing 1,2-divinylcyclododecanol at a temperature less than 400 ° C. under reduced pressure to gasify at least 1,2-divinylcyclododecanol in advance, introducing the gas into a reaction zone kept at 400 to 650° C. under reduced pressure and cooling the reacted gas flowing out of the reaction zone once the reaction is completed.

According to a third embodiment of the present invention, in comparison with the above first and second embodiments, the pressure is set to be lower than the saturated vapor pressure of 1,2-divinylcyclododecanol, for instance, equal to or lower than 5 mm Hg.

According to a fourth embodiment of the present invention, in contrast with the above second and third embodiments, the gas exiting from the reaction zone is first rectified, then cooled to recover 5-cyclohexadecen-1-one.

According to a fifth embodiment of the present invention, in comparison with the above second to fourth embodiments, 2-vinylcyclododecanone is recovered from the gas exiting from the reaction zone or from crude 5-cyclohexadecen-1-one obtained by cooling the reaction gas, and the recovered 2-vinylcyclododecanone is recycled as the starting material for synthesizing 1,2-divinylcyclododecanol.

According to a sixth embodiment of the present invention, in comparison with the above first to fifth embodiments, a hydrogen halide trapping means is provided between pumping means for reducing the pressure at least in the reaction zone, and the reaction zone, the hydrogen halide trapping means being cooled and containing an alkali metal alcoholate or an alkali metal hydroxide, and the pressure in the reaction zone is reduced through the hydrogen halide trapping means.

According to a seventh embodiment of the present invention, there is provided an apparatus used for producing 5-cyclohexadecen-1-one comprising flashing means for vaporizing a raw material containing at least 1,2-divinylcyclododecanol, reaction means for converting 1,2-divinylcyclododecanol, which is in the vapor phase heated to 400 to 650° C., into 5-cyclohexadecen-1-one, recovery means for recovering the produced 5-cyclohexadecen-1-one and pumping means for reducing the pressures in the flashing means, in the reaction means and in the recovery means.

According to an eighth embodiment of the present invention, in comparison with the above seventh embodiment, the reaction means is filled with a filler.

According to a ninth embodiment of the present invention, differing from the above seventh and eighth embodiments, the apparatus further comprises hydrogen halide trapping means containing an alkali metal alcoholate or an alkali metal hydroxide.

BRIEF DESCRIPTION OF THE DRAWINGS

In the accompanying drawings, there are shown illustrative embodiments of the invention, from which the above and the other objectives, novel features, and advantages will be readily apparent.

In the drawings.

DETAILED DESCRIPTION OF THE INVENTION

The present invention will be explained in detail with reference to the drawings.

Figure 1:
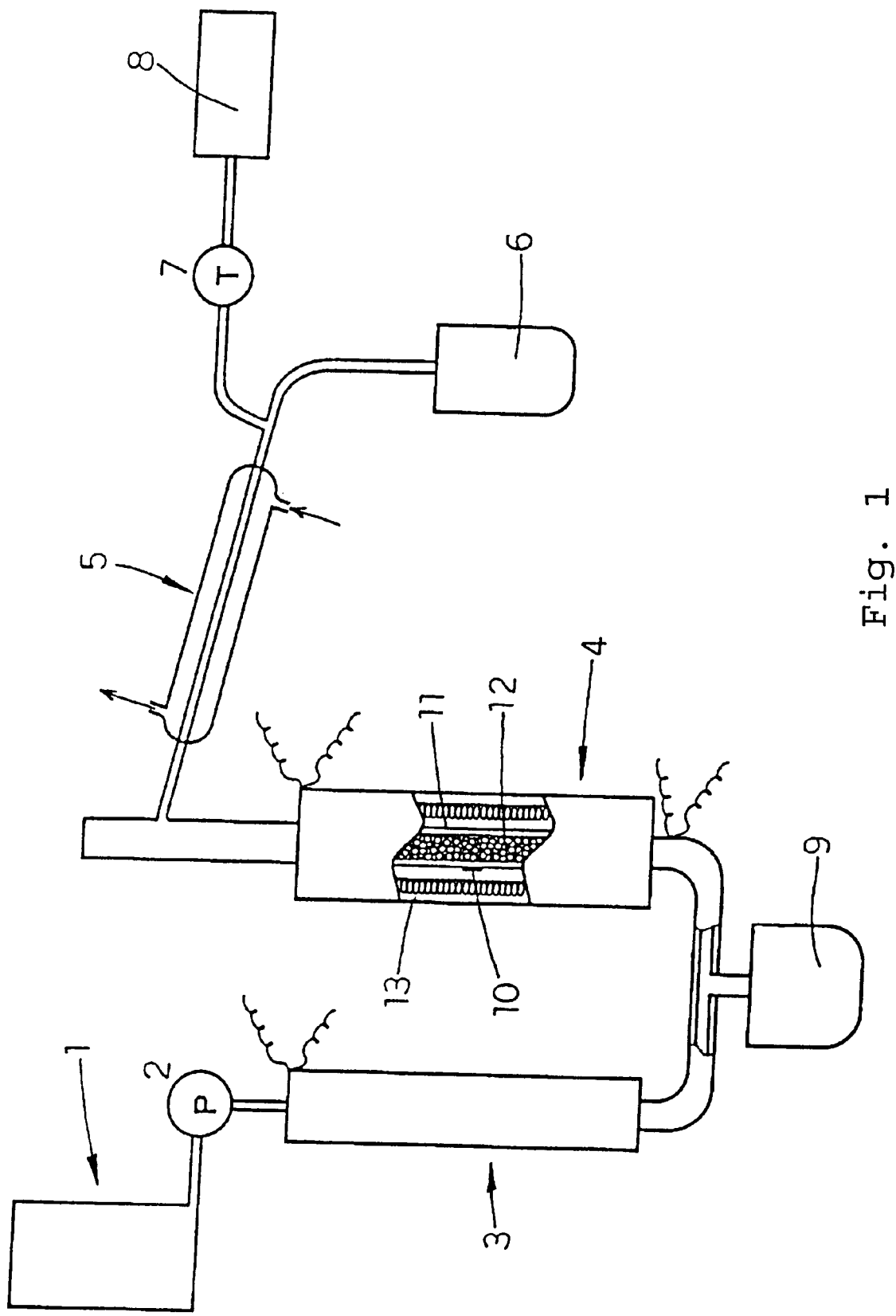
FIG. 1 is an embodiment of an apparatus for the production of 5-cyclohexadecen-1-one according to the present invention.

FIG. 1 shows an embodiment of the apparatus of the present invention. In FIG. 1, the numeral 1 represents a raw material container, 2 a dosage pump, 3 a flash unit for gasification, 4 a reactor, 5 a cooler, 6 a reaction product-recovery container, 7 a hydrochloric acid-trapping unit, 8 a pumping unit, and 9 a non-vaporized product-recovery container. The flash unit 3, the reactor 4 and the reaction product-recovery container 6 are simultaneously set into vacuo by pumping means 8. 1,2-Divinylcyclododecanol used as a starting material may be either a refined material or an undefined crude material.

First, a starting material, 1,2-divinylcyclododecanol is supplied to the flash unit 3 from the raw material container 1 by using the dosaage pump 2. In the present embodiment, the flash unit 3 is formed of a cylindrical material which is heated by an external heater. The flash unit is heated to a temperature required to vaporize at least 1,2-divinylcyclododecanol at the pressure in the flash unit. The flash temperature is preferably set to be in a range in which unnecessary reactions, e.g., side reactions, do not take place. In the present invention, the temperature of the reaction zone is set to be 400° C. or more as will be mentioned later. The flash temperature is therefore limited to 400° C. or less. A preferable temperature is, though it varies depending on the degree of reduced pressure, usually 150 to 250° C., more preferably 200 to 250° C. under a pressure of 2 mm Hg or less. The flash unit 3 may be filled with a filler having a desired form, such as a ball form or a hollow form, to increase the heat efficiency or heat capacity in the flash unit 3.

When the reaction raw material 1,2-divinylcyclododecanol is continuously introduced to the flash unit 3 from the raw material container 1 by the dosage pump 2, 1,2-divinylcyclododecanol is instantly flashed and the flashed material is fed to the reactor 4. Materials which are not flashed under the temperature and pressure conditions in the flash unit 3 are recovered in the non-flashed product-recovery container 9 disposed between the flash unit 3 and the reactor 4. It is desirable that the recovered impurities and polymers contained in the raw material be optionally withdrawn from the non-flashed product-recovery container 9. Incidentally, if flashing of 1,2-divinylcyclododecanol is desired, use of the flash unit may not be required, and the raw material 1,2-divinylcyclododecanol maybe directly heated under reduced pressure so as to be flashed. Also, the non-flashed product-recovery container 9 may be provided with the function of a flashing unit, so that the flash unit and the non-flashed product-recovery unit are integrally formed.

In the present invention, the flashing of 1,2-divinylcyclododecanol, the oxy-cope reaction and the recovery of 5-cyclohexadecen-1-one are usually performed under the same pressure. Accordingly, the pressure under which the raw material is flashed is usually also suitable for the reaction zone, i.e., a degree of reduced pressure lower than the saturated vapor pressure of 1,2-divinylcyclododecanol, for instance, 5 mm Hg or less, preferably about 0.1 to 2 mm Hg and more preferably about 0.2 to 1 mm Hg.

The reactor 4 is used to provide a reaction zone for 1,2-divinylcyclododecanol which is flashed into a vapor phase. Though no particular limitation is imposed on the shape of the reactor itself, a tubular reactor (reaction tube) 11 is commonly used. Any material may be used as the material constituting the reactor 4 as far as it can stand high temperature reactions under reduced pressure and does not adversely affect the reaction. A slight amount of chloride impurities often contaminate the raw material of this reaction. Accordingly, during the reaction, removal of hydrogen chloride takes place and produces hydrochloric acid. It is hence desirable to use a material which is not damaged by an acid. Examples of such a material include copper, copper alloys, industrial nickel, Ni—Cr—Mo alloys, gold, silver, tantalum, stainless, and non-metallic materials such as glass, quartz and carbon. Among these materials, heat-conductive metals having superior mechanical strength are preferred. When a tubular material is used for the reactor, a material having an inner diameter of about 5 to 200 mm and a length of about 50 to 3000 mm is used. The reactormaybe, if necessary, filled with a filler 12 to improve the heat efficiency of the reactor and to produce the effect of uniformly heating the reactor. Any material can be used as the filler insofar as it can improve the heat efficiency of the reactor, produce the effect of heating the reactor uniformly and form an appropriately continuous space within the reactor. Given as examples of the filler are metallic spherical materials, such as ball bearings, having a suitable size, and fillers commonly used for distillation columns, such as Helipack (manufactured by Tokyo Tokushu Kanaami Kabushiki Kaisha) and Sulzer Packing (manufactured by Sumitomo Heavy Industries, Ltd.).

The reactor 4 is heated from the outside by well-known heating means such as heating members, i.e., a ribbon heater and a mantle heater. The temperature of the reaction zone, namely, the temperature in the reactor is measured by a thermometer 10 disposed on the outside wall of the reaction tube 11 in the vicinity of the central portion of the reaction zone.

The temperature in the reactor may suffice to be in a range of temperature at which the purpose of the present invention can be attained. A preferable temperature in the reactor varies depending on various conditions such as the pressure level in the reactor, the shape, length and tube diameter of the reactor, and the amount of the raw material to be supplied. Hence there are no specific limitations as to the temperature. However, a preferable temperature ranges from 400 to 650° C. under a reduced pressure as low as 5 mm Hg or less. When the reaction temperature is lower than 400° C., the rate of the conversion of 1,2-divinylcyclododecanol into 5-cyclohexadecen-1-one tends to be reduced because of slow reaction rate. Hence the efficiency becomes industrially non-feasible. On the other hand, when the temperature exceeds 650° C., the yield of 5-cyclohexadecen-1-one tends to be lowered due probably to decomposition or side reactions. Hence this condition is considered to be impractical.

Though the heat-treatment time varies depending on the pressure level, the heating temperature and the like, the reaction usually takes place in a short time. The amount of the raw material to be supplied varies depending on the diameter, length, heating temperature and pressure level of the reactor. For instance, when a tubular material with a diameter of about 25 mm is used for the reactor, the feed rate is generally in the order of 30 g/5 min, though it may be greater or smaller than this figure.

The reaction product is removed from the top of the reactor 4 and is cooled by the cooler 5 to recover 5-cyclohexen-1-one together with unreacted raw materials including 2-vinylcyclododecanone in the recovery container 6. 2-Vinylcyclododecanone, though unstable in a liquid phase reaction, can be recovered almost quantitatively in the process of the present invention. The present invention has merits in that 2-vinylcyclododecanone can be separated more easily than in the case of separating 2-vinylcyclododecanone from the raw materials including 1,2-vinylcyclododecanol because 5-cyclohexadecen-1-one has a higher boiling point than 1,2-divinylcyclododecanol. Moreover, since the reaction is a vapor phase reaction, an expensive solvent is not required, hence production efficiency per volume is remarkably improved compared with that obtained in a liquid phase reaction. Further, because the process of the present invention also includes crude distillation so that the distillate contains no high-boiling point products, 1,2-divinylcyclododecanol can be easily separated. The highest merit of the present invention is that 5-cyclohexandecen-1-one can be continuously produced, so that a completely automated operation can be achieved.

Furthermore, in the present invention, a separating and refining step may be provided in succession to the reaction step using the reactor so as to perform the separation and recovery of the reaction mixture. In the separation of the reaction mixture, a distillation method is usually used. In the case of a large scale industrial production, it is desirable to adopt a continuous distillation process suitable for automation. In one example of such a continuous distillation process, four distillation columns are used. For each column, a pre-distillate, 2-vinylcyclododecanone, an intermediate distillate and 5-cyclohexadecen-1-one are recovered respectively from each column top. A distillate residue is obtained from the bottom of the last and fourth columns. 2-Vinylcyclododecanone thus separated and recovered is returned to the Grignard reaction step, whereas 5-cyclohexadecen-1-one is obtained as a product either as it is or through further refining steps such as a distillation step and a crystallization step. In these separation and refining steps, a usual refining tower with about 10–40 stages may be used.

Incidentally, the separation and refining of the reaction mixture is not necessarily carried out in succession following the reaction. Specifically, the reaction mixture removed from the reactor is once cooled to obtain a reaction mixture solution, i.e., crude 5-cyclohexadecen-1-one solution. Then the crude 5-cyclohexadecen-1-one solution may be subjected to a distillation process such as described above so as to separate 2-vinylcyclododecanone and 5-cyclohexadecen-1-one. These products are treated in the same manner as above, i.e., 2-vinylcyclododecanone is returned to the Grignard reaction step and is used as the synthetic starting material for 1,2-divinylcyclododecanol whereas 5-cyclohexadecen-1-one is obtained as a product either as it is or through further refining steps such as a distillation step and a crystallization step.

The flash unit 3, the reactor 4 and the recovery container 6 are entirely set under a vacuum by the pumping unit 8, e.g., a vacuum pump. When halides, such as chloride impurities, are present in the raw material, a dehydrochlorination reaction takes place and the generated hydrochloric acid tends to damage the pumping unit 8. In order to prevent such a phenomenon, it is preferable to carry out pressure reduction through a hydrogen halide trap, e.g., a hydrochloric acid trap. As the hydrogen halide trap, it is desirable to use those containing a cooled alkali metal alcoholate or alkali metal hydroxide, for instance, sodium methylate/methanol which is cooled to −78 to −100° C. by using an acetone dry ice bath or liquid nitrogen. This ensures that the entire apparatus can be kept under a high vacuum without any damage to the pumping unit.

1,2-Divinylcyclododecanol which is used as the reaction raw material in the present invention can be produced using various methods. As mentioned above, an excess Grignard's reagent is generally used to carry out a Grignard reaction of 1-chlorocyclododecanone (2) with the Grignard's reagent to produce 2-vinylcyclododecanone (5) via a heating-transfer reaction. Then 2-vinylcyclododecanone (5) is reacted with the remaining Grignard's reagent to produce 1,2-divinylcyclodecanol (3). These steps are usually performed in one pot and the reaction products are washed with acid medium, e.g., acidic water, followed by extractionwith toluene. The extract is washed with a slight amount of an aqueous 1 to 50% NaOH solution, dried, filtered, and condensated to obtain crude 1,2-divinylcyclododecanol.

The resulting crude 1,2-divinylcyclododecanol contains, other than the objective 1,2-divinylcyclododecanol, various compounds such as 2-vinylcyclododecanone which has not reached the final product stage and its isomers, by-products of chlorides, vinyl chloride-Grignard adducts and other high-boiling point compounds. This crude 1,2-divinylcyclododecanol usually contains about 50% by weight of 1,2-divinylcyclododecanol. Then vacuum distillation is performed to obtain refined 1,2-divinylcyclododecanol. In the following examples, unrefined crude 1,2-divinylcyclododecanol is used. However, even if refined 1,2-divinylcyclododecanol is used, 5-cyclohexadecen-1-one can be obtained in a similar way.

EXAMPLES

The present invention will be hereinafter explained in more detail by way of examples which are not intended to limit the present invention.

Example 1

A 50 μl distillation flask was charged with 20 g of crude 1,2-divinylcyclododecanol as starting material and was set in a stainless reactor having a column length of 150 mm and a column diameter of 25 mm, the reactor being filled with Heliopack No. 4. The pressure of the entire apparatus was reduced to 0.5 to 0.2 mm Hg and the flask charged with starting materials was heated to 130 to 150° C. to vaporize 1,2-divinylcyclododecanol. The reactor was heated to 450 to 500° C. using a ribbon heater, such that the temperature of the column top becomes from 115 to 120° C. Usual vacuum distillation was carried out to obtain a distillate. Few decomposed products were found in the distillate. The distillate was subjected to vacuum distillation to obtain 5-cyclohexadecen-1-one and 2-vinylcyclododecanone. The theoretical yield of 5-cyclohexadecen-1-one from 1,2-divinylcyclododecanol was 87.5% (conversion rate: 100%). The aforementioned heating temperature is the temperature in the central portion of the outside of the reactor (11).

Example 2

Figure 2:
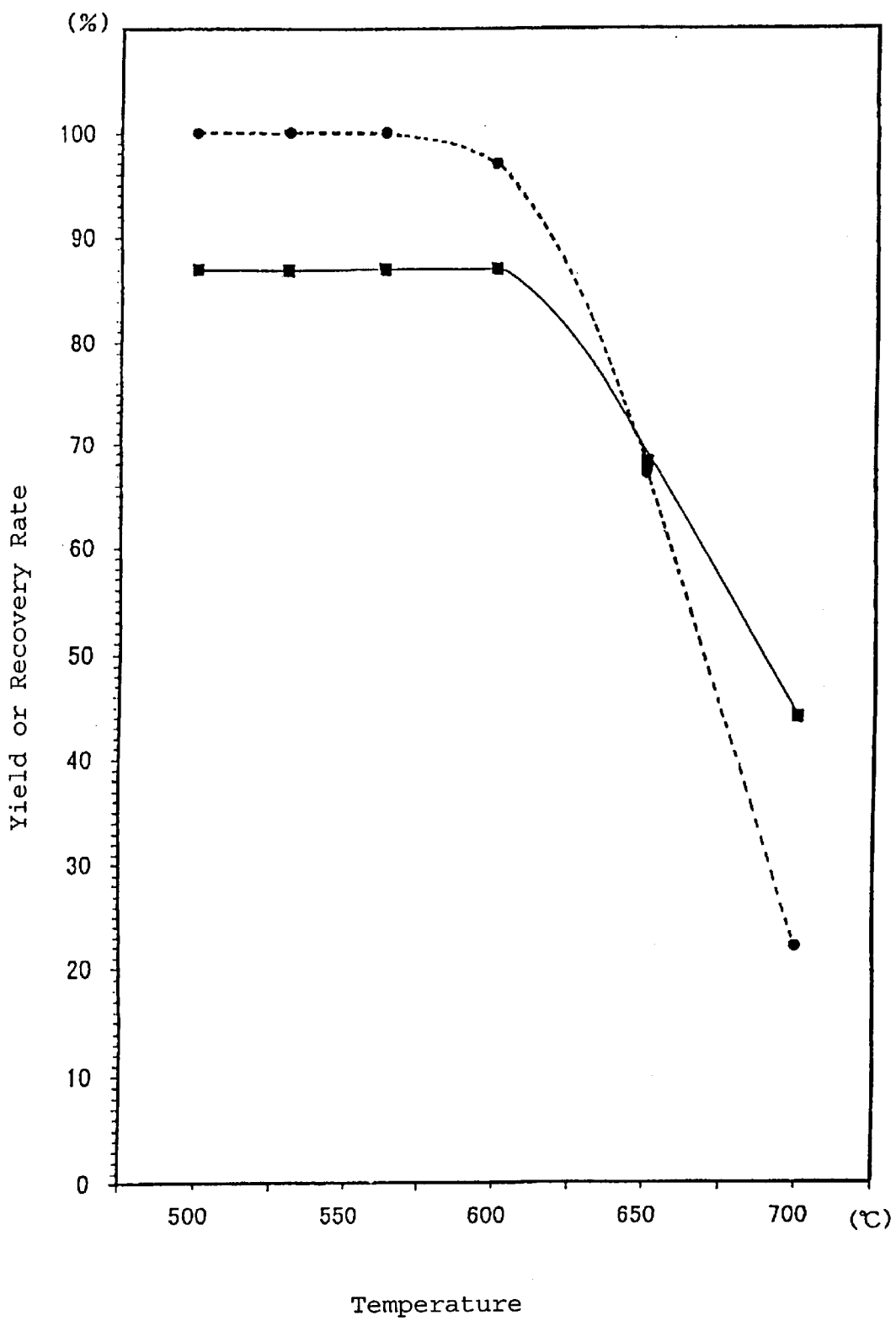
FIG. 2 is a graph showing the yield (■) of 5-cyclohexadecen-1-one and the recovery rate (●) of 2-vinylcyclododecanone in the case where the heating temperature of a reactor is changed.

Using the apparatus shown in FIG. 1, 5-cyclohexadecen-1-one was continuously produced. First, raw materials were supplied to the flash unit 3 from the reaction raw material container 1 by a dosage pump 2 at a rate of 6 g/minute. The flash unit was formed of a stainless cylinder having an inside diameter of 25 mm and a length of 250 mm, was filled with Heliopack No. 4 and was heated at 200 to 250° C. by a ribbon heater. This heating was continuously performed from the outlet of the flash unit to the inlet of the reactor 4. The reactor 4 which was formed of a stainless cylinder having an inside diameter of 25 mm and a length of 400 mm, was filled with 165 ml of Heliopack No. 4, and was heated from its periphery by a 250 mm long mantle heater. At the same time, the pressure of the entire apparatus was reduced to 0.5 mm Hg by the vacuum pump 8. The reactor 4 was heated such that the surface temperature of the outside of the reactor tube (11) in the center portion thereof became 500° C., 530° C., 560° C., 600° C. and 650° C., respectively. The readings were performed at each temperature, and the products formed were recovered. FIG. 2 shows a graph showing the yield of 5-cyclohexadecen-1-one and the recovery rate of 2-vinylcyclododecanone at each temperature. In FIG. 2, ■ indicates the yield of 5-cyclohexadecen-1-one and ● indicates the recovery rate of 2-vinylcyclododecanone. As shown in FIG. 2, the yield of 5-cyclohexadecen-1-one and the recovery rate of 2-vinylcyclododecanone at temperatures ranging from 500 to 600° C. are about 87% and about 100% respectively. By contract, the yield of 5-cyclohexadecen-1-one and the recovery rate of 2-vinylcyclododecanone at 650° C. are 68% and 66% respectively.

Comparative Example

The same procedures as in EXAMPLE 2 were carried out except that the heating temperature was changed to 700° C. The results are shown in FIG. 2. The yield of 5-cyclohexadecen-1-one and the recovery rate of 2-vinylcyclododecanone are 44% and 23% respectively.

In this COMPARATIVE EXAMPLE, the pressure level was found to be 4.1 mm Hg, due probably to decomposition.

As stated above, the production method and the production apparatus according to the present invention make it possible to obtain the following effects.

(1) Since the conversion from 1,2-divinylcyclododecanol to 5-cyclohexadecen-1-one is carried out in a vapor phase condition under a high degree of vacuum, the intermolecular distance is larger than in the case of liquid phase reaction and hence side reactions, such as intermolecular polymerization, do not take place whereby 5-cyclohexadecen-1-one can be obtained in a short time in high yield without side reactions.

(2) Since no solvent is used in the reaction and distillation is carried out simultaneously with the reaction, no after treatment, such as distillation for the removal of pitches and recovery of solvents, is required. Also, a continuous operation is rendered possible, enabling large-scale production and automation (fully automated operation), showing that the production method and apparatus of the present invention are industrially advantageous.

(3) Even when a crude product is used as the reaction starting material, side reactions such as the decomposition and isomerization of useful compounds, e.g., 2-vinylcyclododecanone, are not caused. Hence the unreacted useful compounds can be re-used to obtain approximately 100% of a recovery rate.

What is claimed is:

1. A process for producing a 5-cyclohexadecen-1-one comprising heating 1,2-divinylcyclododecanol in a vapor phase state at 400 to 650° C. Under reduced pressure.

2. A process for producing a 5-cyclohexadecen-1-one comprising heating a liquid raw material containing 1,2-divinylcyclododecanol at a temperature of from 150° C. to less than 400° C. Under reduced pressure to flash the 1,2-divinylcyclododecanol, introducing the flashed 1,2-divinylcyclododecanol into a reaction region kept at 400 to 650° C. under reduced pressure and cooling the reaction gas flowing out of the reaction region after the reaction is completed.

3. A process for producing a 5-cyclohexadecen-1-one according to claim 1, wherein said pressure is set to be 0.1 mm to less than 5 mm Hg.

4. A process for producing a 5-cyclohexadecen-1-one according to claim 2, wherein the reaction gas flowing out of the reaction region is first refined, then cooled to recover 5-cyclohexadecen-1-one.

5. A process for producing a 5-cyclohexadecen-1-one according to claim 2, wherein 2-vinylcyclododecanone is recovered from the reaction gas flowing out of the reaction region or from crude 5-cyclohexadecen-1-one obtained by cooling the reaction gas and the recovered 2-vinylcyclododecanone is recycled as the raw material for synthesizing 1,2-divinylcyclododecanol.

6. A process for producing a 5-cyclohexadecen-1-one according to claim 1, wherein a trapping means for trapping hydrogen halide is provided between the reaction zone and a pumping means for reducing the pressure at least in the reaction zone, the trapping means containing an alkali metal alcoholate or an alkali metal hydroxide and being cooled, and the pressure in the reaction zone is reduced through the trapping means.

7. An apparatus used for producing 5-cyclohexadecen-1-one comprising flashing means for vaporizing a raw material containing at least 1,2-divinylcyclododecanol, reaction means for converting 1,2-divinylcyclododecanol, in a vapor phase reaction, into 5-cyclohexadecen-1-one, recovering means for recovering the produced 5-cyclohexadecen-1-one and pumping means for reducing the pressures in said flashing means, reaction means and recovering means.

8. An apparatus used for producing 5-cyclohexadecen-1-one according to claim 7, wherein said reaction means is filled with a filler.

9. An apparatus used for producing 5-cyclohexadecen-1-one according to claim 7, the apparatus further comprising trapping means for trapping hydrogen halides, the trapping means containing an alkali metal alcoholate or an alkali metal hydroxide.

10. A process for producing a 5-cyclohexadecen-1-one according to claim 2, wherein said pressure is set to be 0.1 mm to less than 5 mm Hg.

11. A process for producing a 5-cyclohexadecen-1-one according to claim 3, wherein the reaction gas flowing out of the reaction region is first refined, then cooled to recover 5-cyclohexadecen-1-one.

12. A process for producing a 5-cyclohexadecen-1-one according to claim 10, wherein the reaction gas flowing out of the reaction region is first refined, then cooled to recover 5-cyclohexadecen-1-one.

13. A process for producing a 5-cyclohexadecen-1-one according to claim 3, wherein 2-vinylcyclododecanone is recovered from the reaction gas flowing out of the reaction region or from crude 5-cyclohexadecen-1-one obtained by cooling the reaction gas and the recovered 2-vinylcyclododecanone is recycled as the raw material for synthesizing 1,2-divinylcyclododecanol.

14. A process for producing a 5-cyclohexadecen-1-one according to claim 4, wherein 2-vinylcyclododecanone is recovered from the reaction gas flowing out of the reaction region or from crude 5-cyclohexadecen-1-one obtained by cooling the reaction gas and the recovered 2-vinylcyclododecanone is recycled as the raw material for synthesizing 1,2-divinylcyclododecanol.

15. A process for producing a 5-cyclohexadecen-1-one according to claim 10, wherein 2-vinylcyclododecanone is recovered from the reaction gas flowing out of the reaction region or from crude 5-cyclohexadecen-1-one obtained by cooling the reaction gas and the recovered 2-vinylcyclododecanone is recycled as the raw material for synthesizing 1,2-divinylcyclododecanol.

16. A process for producing a 5-cyclohexadecen-1-one according to claim 11, wherein 2-vinylcyclododecanone is recovered from the reaction gas flowing out of the reaction region or from crude 5-cyclohexadecen-1-one obtained by cooling the reaction gas and the recovered 2-vinylcyclododecanone is recycled as the raw material for synthesizing 1,2-divinylcyclododecanol.

17. A process for producing a 5-cyclohexadecen-1-one according to claim 12, wherein 2-vinylcyclododecanone is recovered from the reaction gas flowing out of the reaction region or from crude 5-cyclohexadecen-1-one obtained by cooling the reaction gas and the recovered 2-vinylcyclododecanone is recycled as the raw material for synthesizing 1,2-divinylcyclododecanol.

18. A process for producing a 5-cyclohexadecen-1-one according to claim 2, wherein a trapping means for trapping hydrogen halide is provided between the reaction zone and a pumping means for reducing the pressure at least in the reaction zone, the trapping means containing an alkali metal alcoholate or an alkali metal hydroxide and being cooled, and the pressure in the reaction zone is reduced through the trapping means.

19. A process for producing a 5-cyclohexadecen-1-one according to claim 3, wherein a trapping means for trapping hydrogen halide is provided between the reaction zone and a pumping means for reducing the pressure at least in the reaction zone, the trapping means containing an alkali metal alcoholate or an alkali metal hydroxide and being cooled, and the pressure in the reaction zone is reduced through the trapping means.

20. An apparatus used for producing 5-cyclohexadecen-1-one according to claim 8, the apparatus further comprising trapping means for trapping hydrogen halides, the trapping means containing an alkali metal alcoholate or an alkali metal hydroxide.

21. A process for continuously producing 5-cyclohexadecen-1-one y comprising heating 1,2-divinylcyclododecanol in a vapor phase at 400 to 650° C. under reduced pressure.

* * * * *